(12) United States Patent
Tamisiea

(10) Patent No.: US 12,203,865 B2
(45) Date of Patent: Jan. 21, 2025

(54) FLUID TEST DEVICE AND MODULE

(71) Applicant: NEXT PHASE DEVELOPMENT, LLC, West Des Moines, IA (US)

(72) Inventor: Reid Tamisiea, West Des Moines, IA (US)

(73) Assignee: Next Phase Development, LLC, West Des Moines, IA (US)

( * ) Notice: Subject to any disclaimer, the term of this patent is extended or adjusted under 35 U.S.C. 154(b) by 696 days.

(21) Appl. No.: 17/298,681

(22) PCT Filed: Dec. 6, 2019

(86) PCT No.: PCT/US2019/064854
§ 371 (c)(1),
(2) Date: Jun. 1, 2021

(87) PCT Pub. No.: WO2020/118144
PCT Pub. Date: Jun. 11, 2020

(65) Prior Publication Data
US 2022/0042921 A1 Feb. 10, 2022

Related U.S. Application Data

(60) Provisional application No. 62/776,844, filed on Dec. 7, 2018.

(51) Int. Cl.
*G01N 21/78* (2006.01)
*G01N 21/77* (2006.01)
*G01N 33/94* (2006.01)

(52) U.S. Cl.
CPC ............. *G01N 21/78* (2013.01); *G01N 33/94* (2013.01); *G01N 33/9486* (2013.01); *G01N 2021/7759* (2013.01)

(58) Field of Classification Search
CPC .... G01N 21/78; G01N 33/94; G01N 33/9486; G01N 2021/7759; G01N 2021/7796; G01N 21/11
See application file for complete search history.

(56) References Cited

U.S. PATENT DOCUMENTS 5,193,552 A 3/1993 Columbus et al.
2004/0102718 A1 5/2004 Trudeau et al.
(Continued)

OTHER PUBLICATIONS

International Patent Application No. PCT/US2019/064854, International Search Report & Written Opinion mailed Feb. 25, 2020, 9 pages.

*Primary Examiner* — Peter J Macchiarolo
*Assistant Examiner* — John M Royston
(74) *Attorney, Agent, or Firm* — Fredrikson & Byron, P.A.

(57) ABSTRACT

Embodiments for local and safe testing of injection fluids by drawing a sample of injection fluid into a local test chamber while drawing fluid to be tested into a syringe assembly and testing the sample of the injection fluid are disclosed. A fluid test device can include a syringe assembly, a plunger assembly, and a test module. The test module can determine information about fluid in a syringe assembly when the fluid enters a test chamber in the test module. Fluid may enter the test chamber through a one-way valve while a plunger in the plunger assembly is moved in a suction stroke to draw fluid into an interior of the syringe assembly. Fluid may not enter or be expelled from the test chamber when the plunger does not move or is moved in a compression stroke to expel fluid from the syringe assembly.

17 Claims, 9 Drawing Sheets

(56) References Cited

U.S. PATENT DOCUMENTS

| | | |
|---|---|---|
| 2005/0136553 A1 | 6/2005 | Kaylor et al. |
| 2009/0177143 A1* | 7/2009 | Markle .............. A61B 5/14539 604/66 |
| 2014/0186866 A1 | 7/2014 | Duckert et al. |
| 2015/0001071 A1* | 1/2015 | Le Neel .............. G01N 27/3274 204/403.04 |
| 2017/0100070 A1 | 4/2017 | Gupta et al. |

* cited by examiner

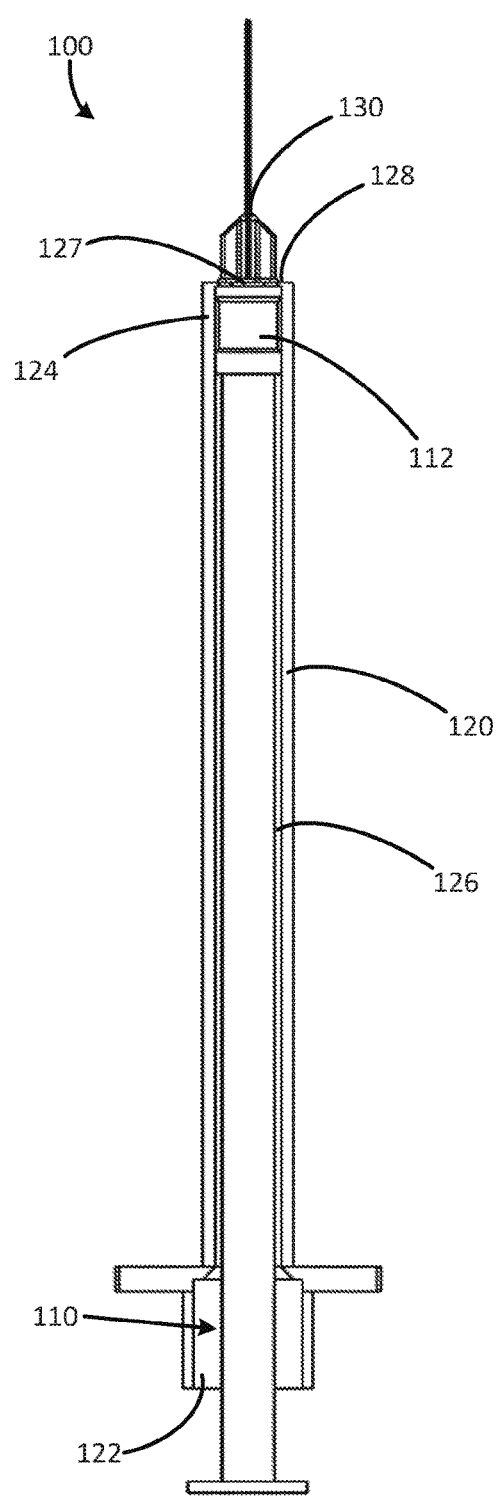 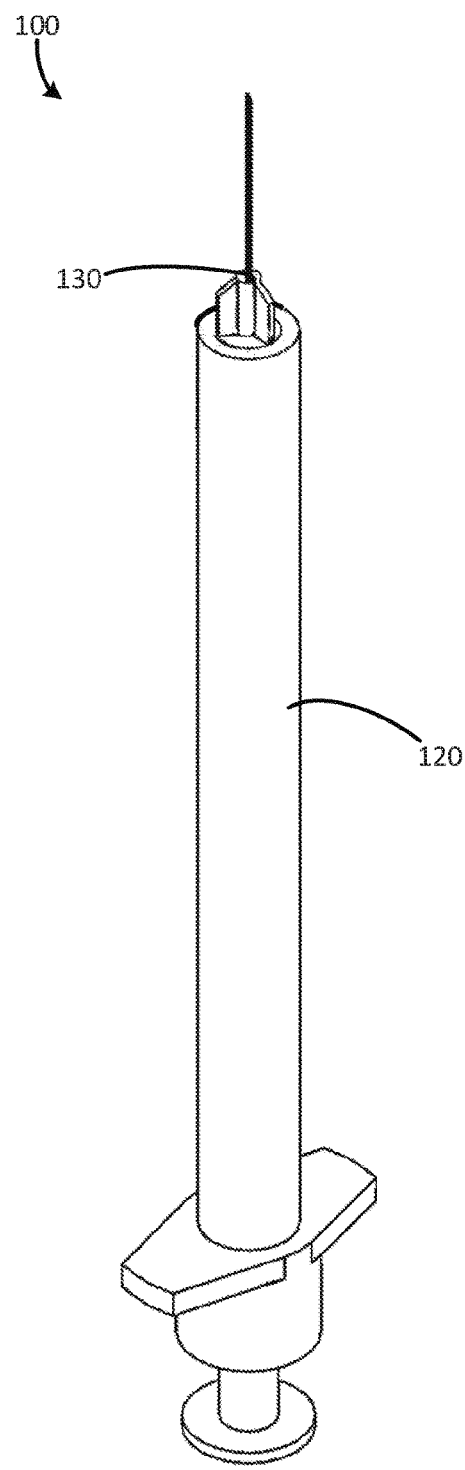
FIG. 1A
FIG. 1B

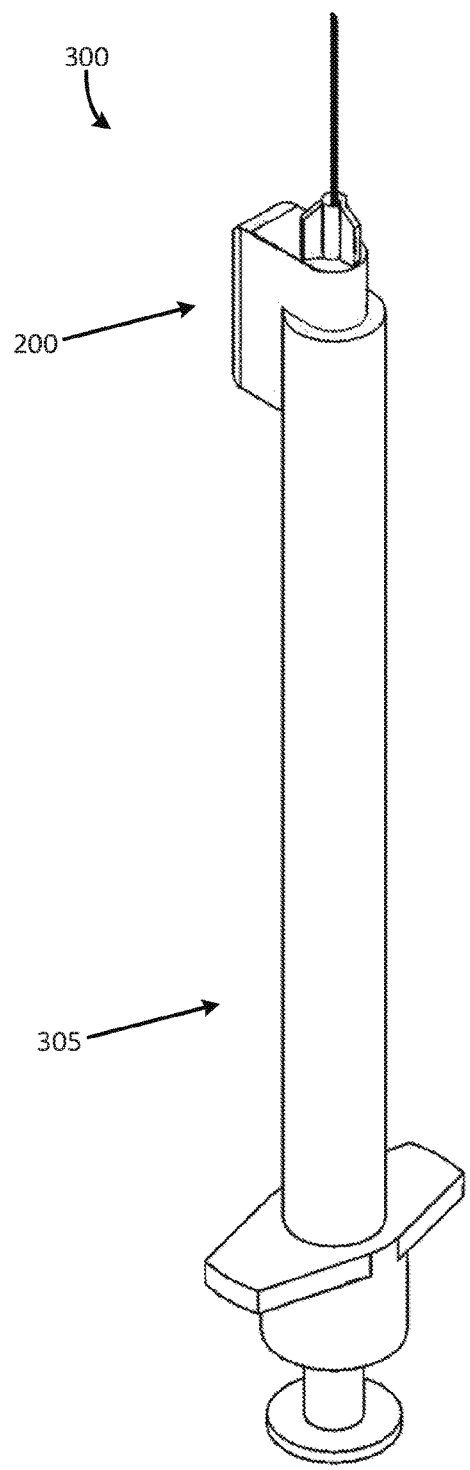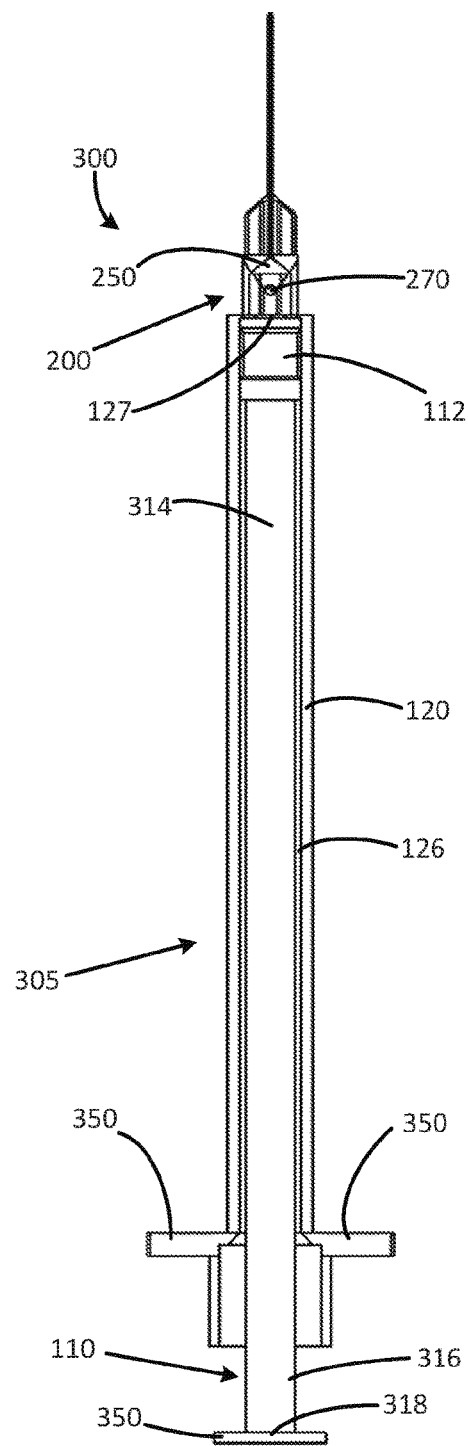
FIG. 3A
FIG. 3B

FLUID TEST DEVICE AND MODULE

The present application is a 35 U.S.C. 371 national phase filing on International Application No. PCT/US2019/064854, filed Dec. 6, 2019, which claims priority to U.S. Provisional Patent Application No. 62/776,844, filed Dec. 7, 2018. The entire contents of each of these applications are incorporated herein by reference.

TECHNICAL FIELD

This disclosure relates generally to the field of medical technology and, more particularly, to devices, systems, and methods for locally testing compositions of fluid in a syringe.

BACKGROUND

Understanding the composition of injectable fluids before administering them provides a safe and effective way to prevent bodily injury. Recently, rising numbers of opioid related incidents led the United States government's Department of Health and Human Services to declare a public health emergency and announce a strategic plan for combatting the "Opioid Crisis." Rising numbers of opioid prescriptions coupled with their addictive nature have led to widespread use and availability of opioids along with an increased number of users who become addicted to them. The Opioid Crisis has negatively impacted public health and social and economic welfare including healthcare costs, addiction treatments, and criminal justice involvement. Attributes of the Opioid Crisis include increased abuse and misuse of prescription and non-prescription opioids resulting in overdoses or withdrawals, for example, in newborns that were exposed to opioids during pregnancy. Increased risks of abuse and misuse occur when the source and composition of the injection fluid is unknown, for instance, where injection fluids such as medications, vaccines, or other drugs are unknowingly laced with opioids or are administered in an uncontrolled or unmeasured fashion. Of particular concern are unregulated drugs that have been unknowingly laced with fentanyl.

Despite their low cost and effectiveness, traditional test methods, such as pre-injection tests, present several challenges for safe administration of injection fluids. Traditional tests may come in a variety of forms including test strips, separation tests, and drip tests. Performing the test typically requires one or more additional pieces of equipment separate from the syringe. In addition to more equipment, the tests can take significant time to complete as many traditional tests require assembly time for separate equipment or settling time to dilute samples. Such samples may become contaminated, requiring repeating the process with a new sample.

SUMMARY

There remains a need for a safe and effective way to perform local pre-injection tests without the need for additional pieces of equipment separate from the syringe itself.

Embodiments disclosed in this document locally and safely test injection fluids by drawing a sample of the injection fluid into a local test chamber while drawing the injection fluid into the syringe and testing the sample of the injection fluid. A check valve can be configured to open, allowing fluid into a test chamber, while a plunger in the barrel of the syringe moves to draw fluid into the syringe. The check valve can be configured to close, preventing fluid from entering the test chamber, while the plunger does not move or moves to expel fluid from the syringe. The test chamber can be included in a test module connectible to the syringe. A portion of the test module can be connectible to an adapter (e.g., a nozzle, a needle, etc.) for directing and controlling fluid flow rate and form in a variety of applications.

One exemplary embodiment includes a fluid test device that includes a syringe, a test module connectible to the syringe, and a test medium. The test module includes a test chamber, and the test medium is contained in the test chamber. In some embodiments, the test chamber can be selectively sealable so as to contain the test medium in the test chamber. The syringe includes a barrel and a plunger that is movable in the barrel. The syringe is configured to draw a fluid into the barrel when the plunger is moving from a plunger closed position to a plunger open position and is configured to expel fluid from the barrel when the plunger is moving from the plunger open position to the plunger closed position. The test module is configured to receive a sample of the fluid from the syringe as the plunger is moving from the plunger closed position to the plunger open position. When the sample is received by the test module and exposed to the test medium, the test medium is configured to indicate information about the sample.

The test module may have a transparent portion configured to allow viewing of the test medium therethrough. In some embodiments, the test medium may include a test strip configured to detect the presence or concentration of a substance in the sample. For example, at least a portion of the test strip can be configured to change to a color indicative of the presence or concentration of the substance in the sample. In addition or alternatively, the test medium may include an enzyme coating.

The test module can be configured to prevent the sample from exiting the test chamber as the plunger is moving from the plunger open position to the plunger closed position. For example, the test module may include a valve assembly configured to control fluid flow into the test chamber. The valve assembly may be configured to receive the sample from a port in the fluid test device and feed the sample through an aperture in the test chamber.

The valve assembly can include a check valve positioned between the port and the aperture. When the valve assembly is in an open position, the sample may be configured to flow from the port into the test chamber through the aperture. Conversely, when the valve assembly is in a closed position, the sample may be prevented from flowing into the test chamber through the aperture.

When provided, the valve assembly may include a ball, a ball stop, and a funnel having a narrow end and a wide end. The ball can be housed within the narrow end and the wide end of the funnel and may be configured to prevent the fluid from exiting the funnel through the narrow end of the funnel when the fluid pushes the ball toward the narrow end of the funnel.

The fluid test device can further include an adapter. In embodiments of this nature, a portion of the test module may be connectable to the adapter.

The fluid test device may also include a reservoir positioned inside the test module. When provided, the reservoir can be configured to supply the sample to the test chamber.

Another exemplary embodiment includes a method for local testing of an injection fluid. The method includes providing a fluid test device that includes a syringe, a test module, and a test medium. The syringe includes a barrel and a plunger that is movable in the barrel. The test module is connected to the syringe and includes a test chamber. The test medium is contained in the test chamber and indicates information about the sample when the sample is drawn into the test chamber. For example, the test medium may include a test strip that detects the presence or concentration of a substance in the sample. In some embodiments, at least a portion of the test strip changes to a color indicative of the presence or concentration of the substance in the sample. In addition or alternatively, the test medium may include an enzyme coating.

The method further includes moving the plunger toward a plunger open position to draw the injection fluid into the barrel and to draw a sample of the injection fluid into the test chamber. The test module may prevent the sample from exiting the test chamber after the sample is drawn into the test chamber.

The method may further include administering the injection fluid when a concentration of a predetermined substance within the sample is determined to be below a predetermined level. In addition or alternatively, the method may include administering the injection fluid when a predetermined substance is determined to be absent from the sample. The predetermined substance may include at least one of fentanyl and brodifacoum.

Such a fluid test device provides a number of advantages over conventional syringes. The fluid test device can locally and automatically test the concentration of an injection fluid (e.g., opioids) during normal use. Positioning the test module on the syringe removes the need for extra equipment separate from the syringe required for traditional test methods. Further, local testing reduces the risk of contaminating the sample and reduces the amount of time required for setting up the test. Numerous other advantages of such a fluid test device will be apparent to those skilled in the art.

BRIEF DESCRIPTION OF DRAWINGS

The following drawings are illustrative of particular embodiments of the present invention and therefore do not limit the scope of the invention. The drawings are intended for use in conjunction with the explanations in the following description. Embodiments of the invention will hereinafter be described in conjunction with the appended drawings, wherein like numerals denote like elements.

FIG. 1A is a side elevational cross-sectional view of a conventional syringe.

FIG. 1B is a perspective view of a conventional syringe.

FIG. 3A is a perspective view of an illustrative fluid test device with a test module.

FIG. 3B is a back elevational cross-sectional view of an illustrative fluid test device with a test module.

DETAILED DESCRIPTION

Figure 2B:
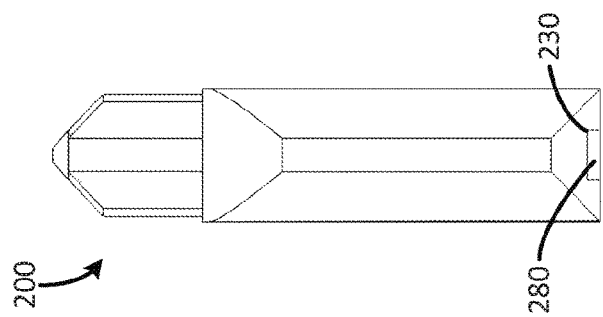
FIG. 2B is a front elevational view of an illustrative test module.

The following detailed description is exemplary in nature and provides some practical illustrations and examples. Those skilled in the art will recognize that many of the noted examples have a variety of suitable alternatives. A number of various exemplary fluid test systems, devices, and techniques are disclosed herein using the description provided as follows in addition to the accompanying drawings. Each of the systems, devices, and techniques disclosed herein can be employed independently or in combination with one or more (e.g., all) of the other systems, devices, and techniques disclosed herein.

The conventional syringe 100 shown in FIGS. 1A and 1B can be used in a variety of applications, especially within the medical field. The conventional syringe 100 shown in FIG. 1A can include a plunger assembly 110, a barrel 120, and an adapter 130. The barrel 120 can include a plunger opening 122 for receiving the plunger assembly 110. The plunger assembly 110 can move reciprocally within the barrel 120 between the plunger opening 122 and a plunger stop 124 positioned opposite the plunger opening 122. The plunger opening 122, barrel 120, and plunger stop 124 can together form an interior 126 of the barrel 120 for holding fluid. The plunger assembly 110 may allow fluid to enter the interior 126 of the barrel 120 between a plunger 112 and the plunger stop 124 and prevent fluid from exiting the interior 126 of the barrel 120 between the plunger 112 and the plunger opening 122.

Movement of the plunger assembly 110 can controllably move fluid into and out of the interior 126 of the barrel 120 through the orifice 127. The barrel 120 of the conventional syringe 100 can include the plunger stop 124 positioned opposite the plunger opening 122. The plunger stop 124 can have a first side 128 and an orifice 127 for receiving and expelling fluid from the barrel 120. When the plunger assembly 110 is actuated within the barrel 120 away from the orifice 127, the orifice 127 can receive and feed fluid into the interior 126 of the barrel 120. When the plunger assembly 110 is actuated within the barrel 120 toward the orifice 127, fluid may be expelled from the interior 126 of the barrel 120 through the orifice 127. An adapter 130 can fit over the orifice 127 via a connector at the first side 128 of the plunger stop 124. The adapter 130 can be readily interchangeable and suitable for expelling fluid, receiving fluid, or both in a desired fashion. Such versatility of the conventional syringe 100 has led to a variety of uses in different applications.

The conventional syringe 100 shown in FIG. 1B has been used in a variety of fashions across a number of different industries. For instance, quick and controlled dosages of fluid (e.g., medicine, vaccines, etc.) can be administered intravenously using the conventional syringe 100 and the adapter 130 in the form of a needle or a tube. A conventional syringe 100 may have a transparent barrel 120 that includes markings for measuring fluid in the interior of the barrel 120, e.g., for measuring dosages or prescriptions. In some instances, the adapter 130 of a conventional syringe 100 can include a nozzle to direct fluid flow (e.g., of iodine, glue, etc.) onto an operating surface. A conventional syringe 100 may also be used to prime tubing lines or remove fluid, e.g., from diseased areas of the body with extraneous fluids. Although the conventional syringe 100 is useful in a variety of applications, it does not include a method or device for locally determining information about the fluid in the interior of the barrel 120.

Figure 2A:
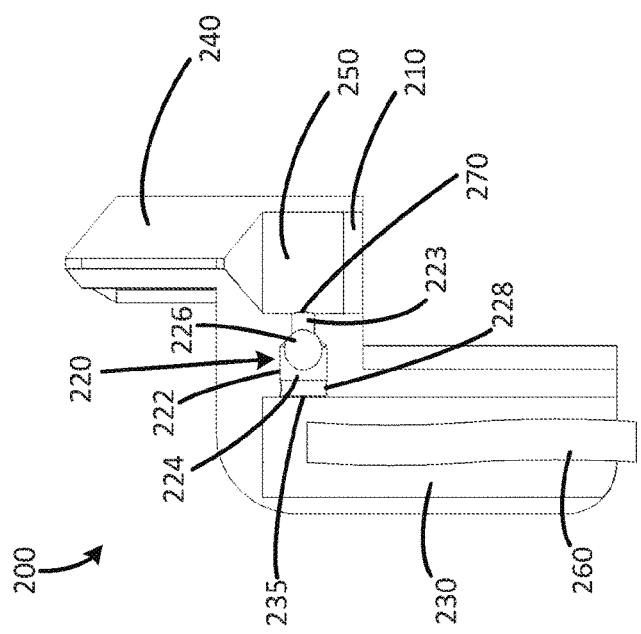
FIG. 2A is a side elevational cross-sectional view of an illustrative test module with a test strip.
Figure 2C:
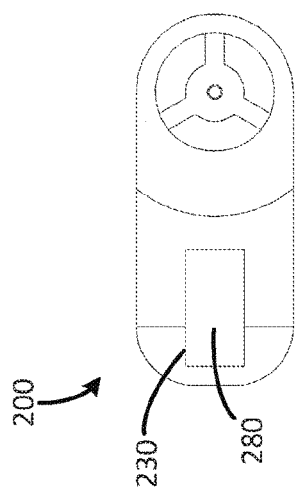
FIG. 2C is a bottom elevational view of an illustrative test module.

An illustrative fluid test device may include a test module 200 as shown in FIGS. 2A-2C configured to receive and test a sample of fluid. The test module 200 can determine information about fluid (e.g., composition, fluid type, acidity levels, etc.) in a syringe assembly, e.g., from receiving fluid from actuating the syringe assembly as discussed in further detail below. The test module 200 can include a coupler 210, a valve assembly 220, a test chamber 230, and a support 240. The coupler 210 can be connectible to the connector of a conventional syringe or a syringe assembly as further discussed below. The support 240 can be similar to the first end of the orifice in that it can be connectible to or otherwise support an adapter (e.g., needle, nozzle, fitting, etc.). In some instances the test module 200 may contain a reservoir 250 that is positioned inside the test module 200 and that can supply fluid to the test chamber 230.

The test chamber 230 may contain a test medium 260 configured to provide indicia of or information about the fluid in the fluid test device. In many instances, the test medium 260 may be a test strip 260 configured to detect the presence or level of a substance in the fluid, e.g., by at least a portion of the test strip 260 turning a certain color indicative of the presence or level of substance (e.g., fentanyl, brodifacoum, and other toxic chemicals). The color, for example, can be matched to an associated chart for interpreting the results from the test medium 260 or can be indicative itself (e.g., red for dangerous levels and green for acceptable levels). In some such cases, the test chamber 230 can include a slot 280, as seen in FIGS. 2B and 2C, for receiving the test strip and an end cap for sealing the test chamber 230. Some embodiments of the test module 200 will have a transparent portion to view the test medium. In certain embodiments, the test chamber 230 may be sealed for containing the test medium that is a testing fluid such as for a separation test. Fluid flow into the test chamber 230 can be controlled by the valve assembly 220.

Referring again to FIG. 2A, the valve assembly 220 can receive fluid from, but not expel fluid through, a port 270 in the fluid test device and feed received fluid to the test chamber 230 via an aperture 235 in the test chamber 230. The aperture 235, in some embodiments, may align with the port 270 (e.g., abutting the port 270, in a channel with the port 270, etc.). In many instances, the valve assembly 220 may be a check valve (e.g., ball check valve, diaphragm check valve, non-return valve, swing check valve, etc.) positioned between the port 270 and the aperture 235. Thus, when the valve assembly 220 is in an open position, fluid may flow from the port 270 and into the test chamber 230 through the aperture 235. In contrast, when the valve assembly 220 is in the closed position, fluid may not flow from the port 270 into the test chamber 230 through the aperture 235. The valve assembly 220 may be in the open position when there is a vacuum in the interior of the barrel. The valve assembly 220 may be in the closed position when there is positive pressure in the interior of the barrel or in the test chamber 230.

In some such embodiments, the valve assembly 220 may include a funnel 222, a ball 226, and a ball stop 228. The funnel 222 may have a narrow end 223 and a wide end 224 and may house the ball 226 therebetween. The narrow end 223 of the funnel 222 can be proximal to the port 270 and the wide end 224 of the funnel 222 can be proximal to the aperture 235 in the test chamber 230. The ball 226 can have a first diameter that may be smaller than the cross-sectional diameter of the narrow end 223 of the funnel 222, the ball stop 228, or both. The first diameter of the ball 226 may not be equal to or larger than the diameter of the wide end 224 of the funnel 222 and, therefore, may be prevented from exiting the funnel 222 through the wide end 224 of the funnel 222 by the ball stop 228 when the ball 226 is pressed against the ball stop 228. Thus, the ball 226 can move within the funnel 222 between the narrow end 223 of the funnel 222 and the ball stop 228.

Movement of the ball 226 within the funnel 222 can control the flow of fluid within the funnel 222. The ball stop 228, for example, may be a narrowing feature or plate positioned outside of the ball 226 at the wide end 224 of the funnel 222. The ball stop 228 may limit movement of the ball 226 in the direction from the narrow end 223 toward the wide end 224 of the funnel 222 while allowing fluid to flow out of the funnel 222. When pressed against the ball stop 228, the ball 226 may form a seal with the ball stop 228 thereby preventing fluid from entering the test chamber 230 through the aperture 235 at the wide end 224. On the other hand, when pressed against the narrow end 223, fluid may be allowed to flow into the funnel 222, e.g., over the ball 226, and into the test chamber 230 through the aperture 235. Thus, as fluid enters the funnel 222 through the narrow end 223 of the funnel 222, fluid can push the ball 226 toward the ball stop 228 at the wide end 224 of the funnel 222 and be prevented from exiting the funnel 222 through the aperture 235. In contrast, as fluid enters the funnel 222 through the wide end 224 of the funnel 222, fluid can push the ball 226 toward the narrow end 223, flow over the ball 226, and flow out of the narrow end 223 of the funnel 222 through the port 270.

The fluid test device 300 shown in FIGS. 3A-3D can include the test module 200 and a syringe assembly 305 connectible to the test module 200. The test module 200 shown in FIG. 3A can receive fluid from the syringe assembly 305, but may not expel fluid into the syringe assembly 305. Fluid received by the test module 200 can be exposed to the test medium in the test chamber to provide or indicate information about the fluid in the syringe assembly 305.

Though depicted at one end of the syringe assembly 305, the test module 200 may be located anywhere on the syringe assembly 305 where it can receive fluid to be tested. For instance, some embodiments of the fluid test device 300 may have the test module 200 positioned anywhere along the barrel 120 (e.g., near the handle, near the adapter, or anywhere in between). In another embodiment, the test module 200 may be positioned between the adapter and the barrel 120. Still in yet another embodiment, the test module 200 may be positioned, e.g., in a fluid line between an injection site and an injection fluid or fluid reservoir.

Components of the fluid test device 300 shown in FIG. 3B can be made of a number of different materials that provide quality construction and facilitate use of the fluid test device 300 in various applications. The barrel 120 in the syringe assembly 305 can comprise plastic or glass and, in many instances, be transparent with markings on the barrel 120 indicating fluid measurements. The plunger 112 may comprise a non-toxic, flexible material (e.g., rubber or synthetic rubber). The test module 200 and components of the plunger assembly 110 can comprise plastic, metal, or both as well as any other suitable rigid material. In many instances, components of the test module 200, the syringe assembly 305, or both may be disposable after one or more uses.

As can be appreciated, though described in connection with a syringe, the fluid test device 300 can be employed by different users in other applications. The test module 200 is suitable for many applications where it is desirable to understand the composition of a fluid. For instance, medical professionals at hospitals, donation sites, etc. can use the test module 200 in connection with plasma needles, blood bank needles, medical pumps, and the like. In the same way, lab technicians may use the test module 200 to test, e.g., for proper organ functioning (e.g., liver, kidney, heart, etc.), blood disorders (e.g., iron deficiency, vitamin D deficiency, etc.), food testing (e.g., starch, fructose, etc.), mineral content (e.g., calcium, phosphate, etc.), and the like. On the other hand, end users may use the fluid test device 300 with the test module 200 to self-administer drugs or prescription medicines.

The fluid test device 300 can be similar to a conventional syringe, including a syringe assembly 305, and may include the port 270. In many embodiments, the port 270 can be a through hole in a component of the fluid test device 300 that is exposed to fluid to be tested, e.g., in the interior 126 of the barrel 120 or in the test module 200. In many embodiments, the port 270 can be in a wall of the reservoir 250 in the test module 200. In some embodiments, the port 270 may be in the barrel 120 of the syringe assembly 305. In some such embodiments, an interior side of the port 270 that faces the interior 126 of the barrel 120 can be exposed to the fluid in the interior 126 of the barrel 120 and an exterior side of the port 270 that faces away from the interior 126 of the barrel 120 can be exposed to the test module 200. The port 270 in an illustrative embodiment may be circular, but may assume any number of shapes and sizes in various embodiments.

Note that, though the port 270 is discussed in connection with the test module 200 and the barrel 120, the port 270 may be positioned anywhere suitable in the fluid test device 300. For instance, the port 270 may extend through the plunger 112 and feed into a fluid line that is connected to the aperture 235 of the test module 200. In another embodiment and in the same way, the port 270 may be in the handle 318 of the fluid test device. In yet another embodiment, the port 270 may be positioned proximal to the orifice 127 (e.g., adjacent to the orifice 127) or be the orifice 127 itself, e.g., which may be connected to one or more fluid lines or fluid paths of which at least one feeds into the test module 200.

Figure 3C:
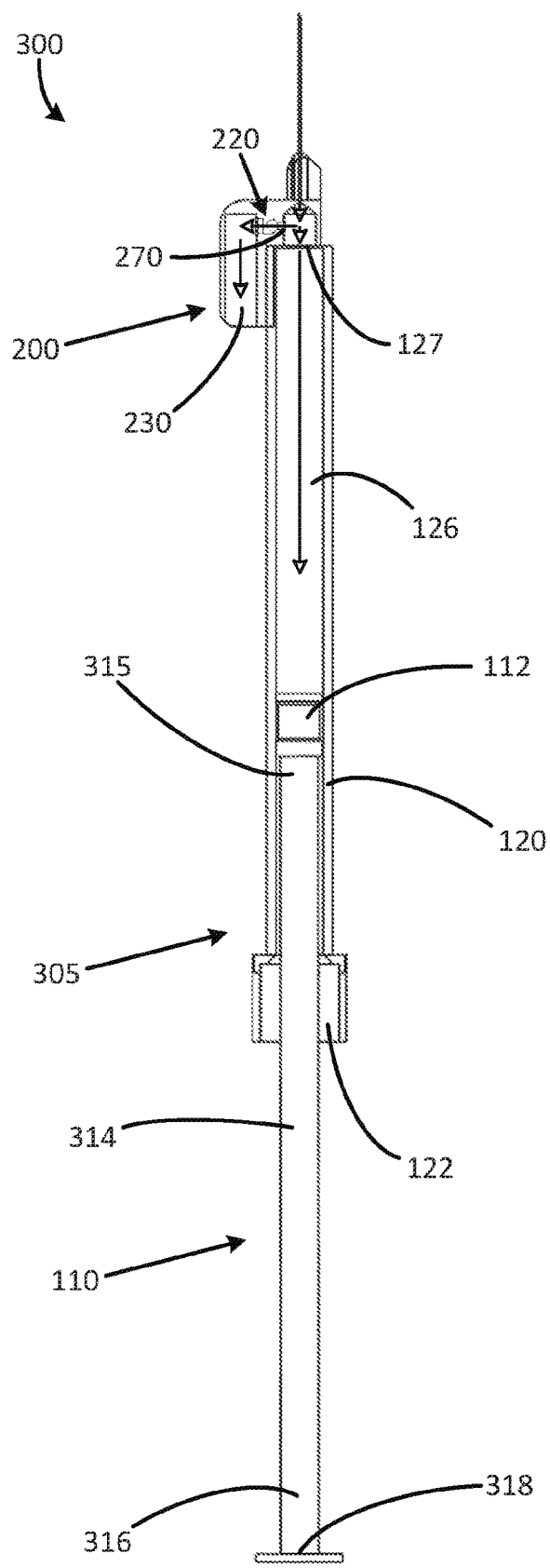
FIG. 3C is a side elevational cross-sectional view of an illustrative fluid test device with a test module and a plunger in a plunger open position.

The plunger assembly 110 as shown in FIG. 3C can be included in the fluid test device 300 and form a tight fit between the plunger 112 and the barrel 120 of the syringe assembly 305. The plunger assembly 110 can include the plunger 112, the plunger shaft 314, and a handle 318. The plunger 112 can be positioned at a plunger end 315 of the plunger shaft 314 and the handle 318 can be positioned opposite the plunger end 315 of the plunger shaft 314 at the handle end 316 of the plunger shaft 314. In some embodiments, the outer diameter of the plunger 112 can be larger than the outer diameter of the plunger shaft 314. In many embodiments, the outer diameter of the plunger 112 can be variable along the direction of a centerline axis through the plunger shaft 314, e.g., to minimize friction between the plunger 112 and the barrel 120. The plunger 112 can be received in the plunger opening 122 of the barrel 120 and form a tight fit within the barrel 120, e.g., such that a hermetic seal is created within the interior 126 of the barrel 120.

The plunger 112 can move within the barrel 120 to receive or expel fluid from the interior 126 of the barrel 120 through the orifice 127. The plunger stop 124 can limit movement of the plunger 112 in the direction toward the orifice 127. In some embodiments, a second plunger stop may be located near the plunger opening 122, enclosing the plunger 112 in the barrel 120 and limiting movement of the plunger 112 in the direction of the plunger opening 122. Movement of the plunger 112 away from the orifice 127 can generate a negative pressure (e.g., a vacuum), thereby allowing fluid to be received in the interior 126 of the barrel 120 through the orifice 127. Movement of the plunger 112 toward the orifice 127 can generate a positive pressure in the interior 126 of the barrel 120, thereby expelling fluid from the interior 126 of the barrel 120 through the orifice 127. Movement of the plunger 112 can be caused by movement of the plunger shaft 314, e.g., at the handle 318 by an operator or by a machine.

Referring again to FIG. 3B, in some embodiments, the handle 318 can be one or more protrusions 350 at the handle end 316 of a plunger shaft 314. The protrusions 350 may be suitably sized to accommodate a human digit (e.g., a finger or a thumb) to operate the handle 318. The handle 318 may also include one or more protrusions 350 in the barrel 120 of the syringe assembly 305, e.g., to provide a stationary support while the plunger 112 is actuated. In many instances, the plunger 112 can be positioned at an end of the barrel 120 positioned opposite of the test module 200 to facilitate operation of the fluid test device 300.

Figure 3D:
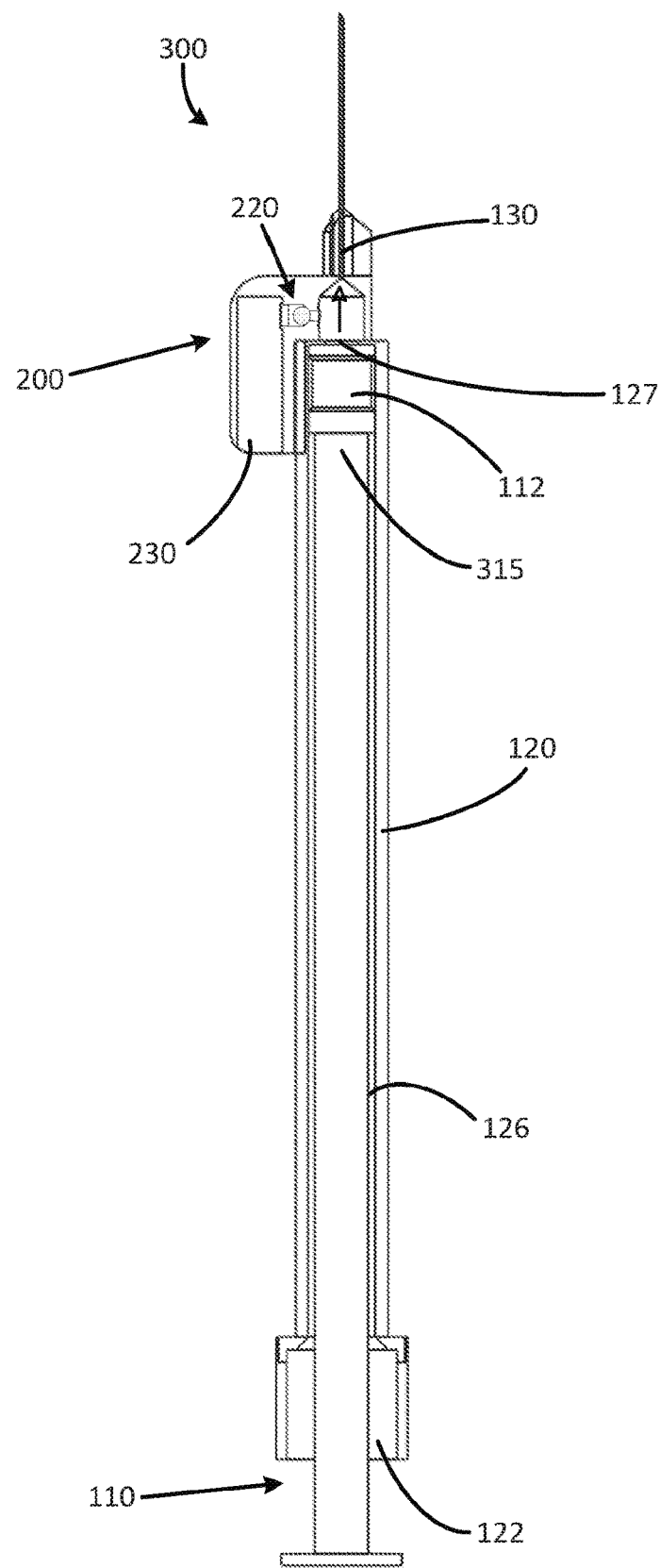
FIG. 3D is a side elevational cross-sectional view of an illustrative fluid test device with a test module and the plunger in a plunger closed position.

Referring to FIGS. 3C and 3D, in operation, the fluid test device 300 can allow fluid to enter or prevent fluid from exiting the test chamber 230 depending on the position of the plunger 112. The plunger 112 in the plunger assembly 110 can move between the plunger open position shown in FIG. 3C and the plunger closed position shown in FIG. 3D. Fluid can be drawn, as indicated by the hollow-tipped arrow, into the test chamber 230 for testing when the plunger 112 is moving to the plunger open position as shown FIG. 3C. The plunger 112 can move from the plunger closed position to the plunger open position via a vacuum stroke thereby creating a negative pressure in the interior 126 of the barrel 120. The valve assembly 220 can be in the open position while the plunger 112 moves away from the orifice 127 and toward the plunger opening 122 in the vacuum stroke. Thus, moving the plunger 112 in the vacuum stroke can, therefore, draw fluid into the test chamber 230 through the port 270 and into the interior 126 of the barrel 120 through the orifice 127.

On the other hand, fluid can be prevented from leaving the test chamber 230 when the plunger 112 is in the plunger closed position as shown in FIG. 3D. The plunger 112 can move from the plunger open position to the plunger closed position via a compression stroke thereby creating a positive pressure in the interior 126 of the barrel 120. In the plunger closed position, fluid may be expelled, as indicated by the hollow-tipped arrow, from the fluid test device 300 through the orifice 127. The valve assembly 220 can be can be in the closed position as the plunger 112 moves in a compression stroke away from the plunger opening 122 and toward the orifice 127. Thus, moving the plunger 112 in a compression stroke can, therefore, prevent fluid from exiting the test chamber 230 while expelling fluid from the interior 126 of the barrel 120 out through the orifice 127 (e.g., through the adapter 130). Such fluid can proceed to flow to a desired application.

Illustrative methods for local testing of an injection fluid are disclosed. The method can include providing a fluid test device similar to those disclosed elsewhere herein. The method can include placing the adapter of the fluid test device into an injection fluid. The method can include moving the plunger in a suction stroke while a tip of the adapter is submerged in the injection fluid. The method can include removing the fluid test device from the injection fluid. The method can include observing and interpreting a test result from a testing chamber in a test module of the fluid test device to determine the composition of the fluid. The method can include administering the injection if the fluid composition is safe and not administering the injection if the fluid is not safe.

Figure 4:
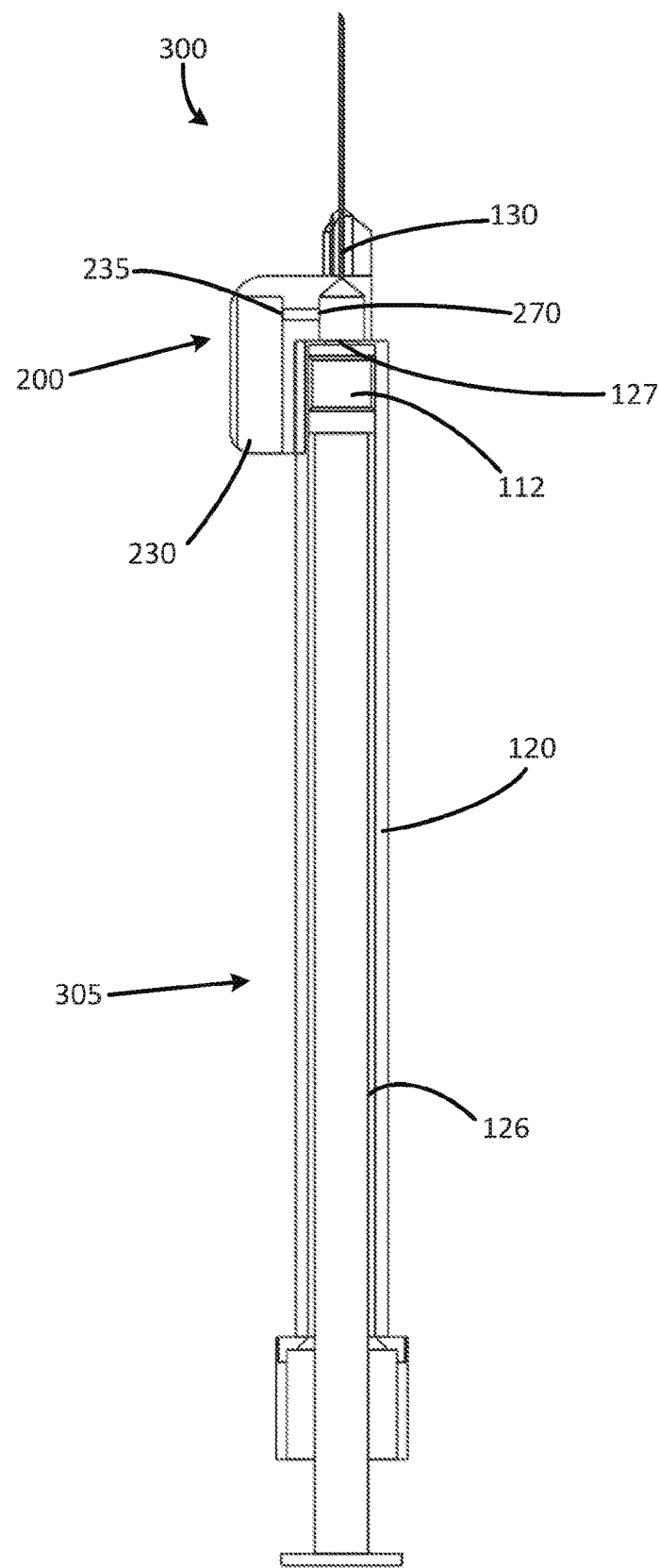
FIG. 4 is a side elevational cross-sectional view of an alternative embodiment of the fluid test device with the plunger in a plunger closed position and with a test module minus a valve assembly.

Several alternative embodiments of the fluid test device are shown in FIGS. 4-7. Certain alternative embodiments may include a system with one or more fluid test devices or test modules. In some instances, alternative embodiments include more than one valve assembly and/or more than one test chamber within the test module. With reference to FIG. 4, the test module 200 in some embodiments may be a test strip, e.g., directly connected to the port 270. Instead of a test strip, the test medium in some embodiments may be an enzyme coating on the interior walls of the test chamber 230 or the barrel 120. In other alternative embodiments, the adapter 130 may include bottle adapters, catheter adapters, cap adapters, or one or more interlocking adapters (e.g., Luer Locks).

Other embodiments may not have a valve assembly at all as shown in FIG. 4. For example, the test medium may not be harmful to the injection fluid or to the subject receiving the injection. Thus, the fluid testing device 300 may be configured to allow some of the test medium to be injected along with the injection fluid after a sample has been tested. For instance, fluid may enter the test chamber 230 when the plunger 112 is moved in a vacuum stroke as described elsewhere herein and may then be allowed to be expelled from the interior 126 of the barrel 120 through the orifice 127.

Figure 5A:
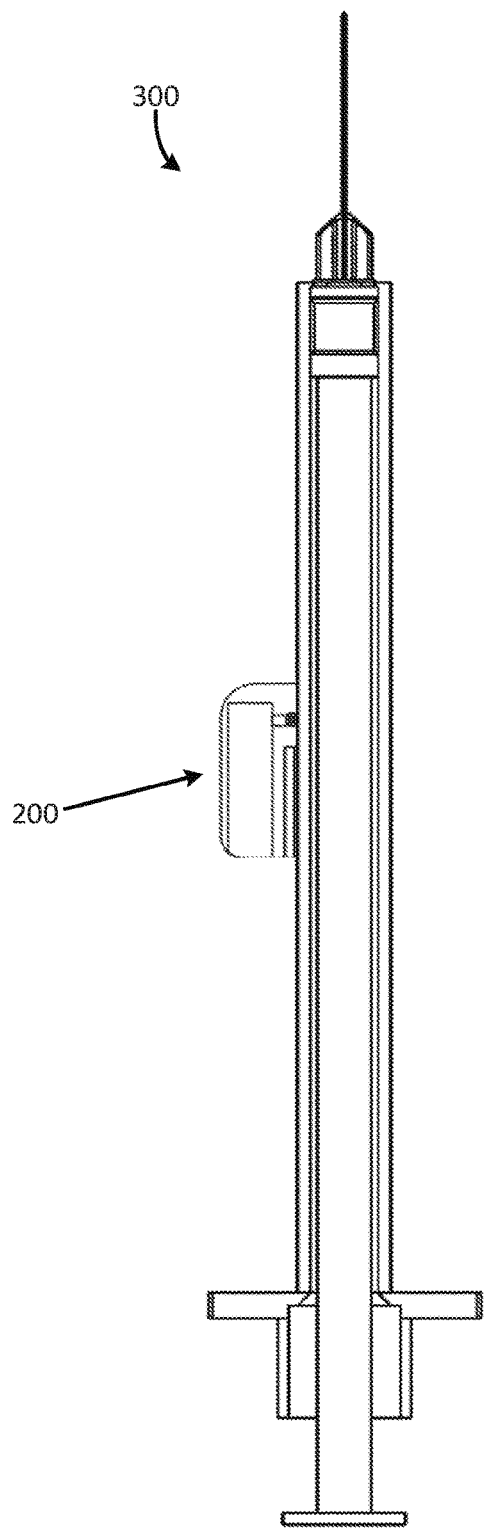
FIG. 5A is a back elevational cross-sectional view of an alternative embodiment of the fluid test device with a test module positioned at the middle of the barrel in a syringe assembly.
Figure 5B:
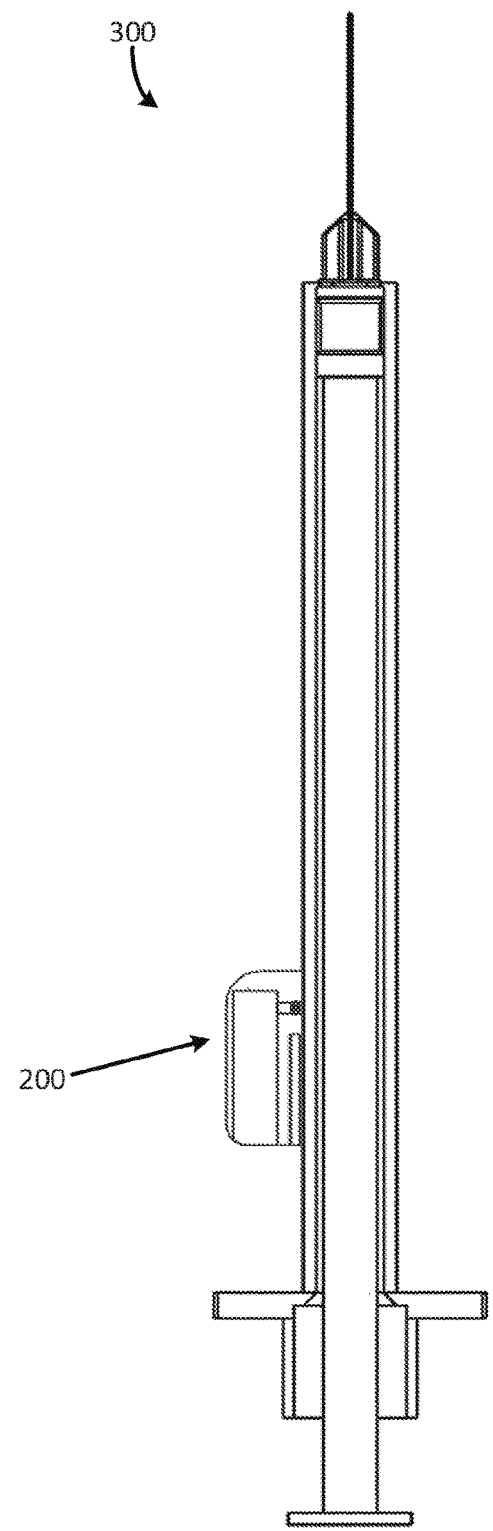
FIG. 5B is a back elevational cross-sectional view of an alternative embodiment of the fluid test device with a test module positioned at the middle of the barrel in a syringe assembly.
Figure 6:
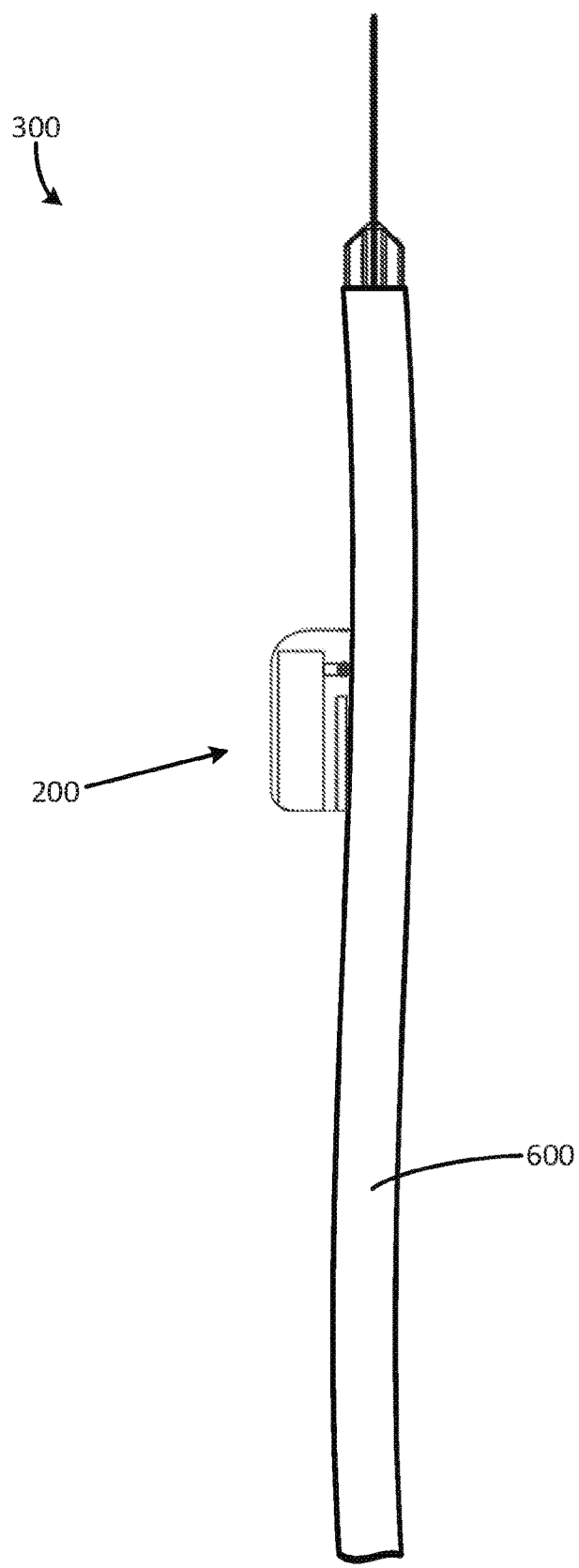
FIG. 6 is a side elevational view of an alternative embodiment of the fluid test device that is a test module in a fluid line.

As mentioned elsewhere herein, some alternative embodiments of the fluid test device 300 may have the test module 200 positioned at different locations along the barrel 120 of a syringe assembly 305 or in the injection system. For instance, in some embodiments, the test module 200 may be positioned in the middle of the barrel 120 as shown in FIG. 5A or at a position that is proximal to the plunger opening of the barrel 120 as shown in FIG. 5B. Some alternative embodiments may not include a plunger, but rather, may have the test module 200 positioned in a fluid line 600 as shown in FIG. 6. In such embodiments, the test module 200 may operate similar to those described elsewhere herein. The test module 200 can be connectible to the fluid line 600 similar to how the test module 200 connects to the syringe assembly. Instead of being controlled by the plunger, movement of the fluid within the fluid line 600, and thereby within the test module 200, may be controlled by a pump, e.g., with a piston or a diaphragm.

Figure 7:
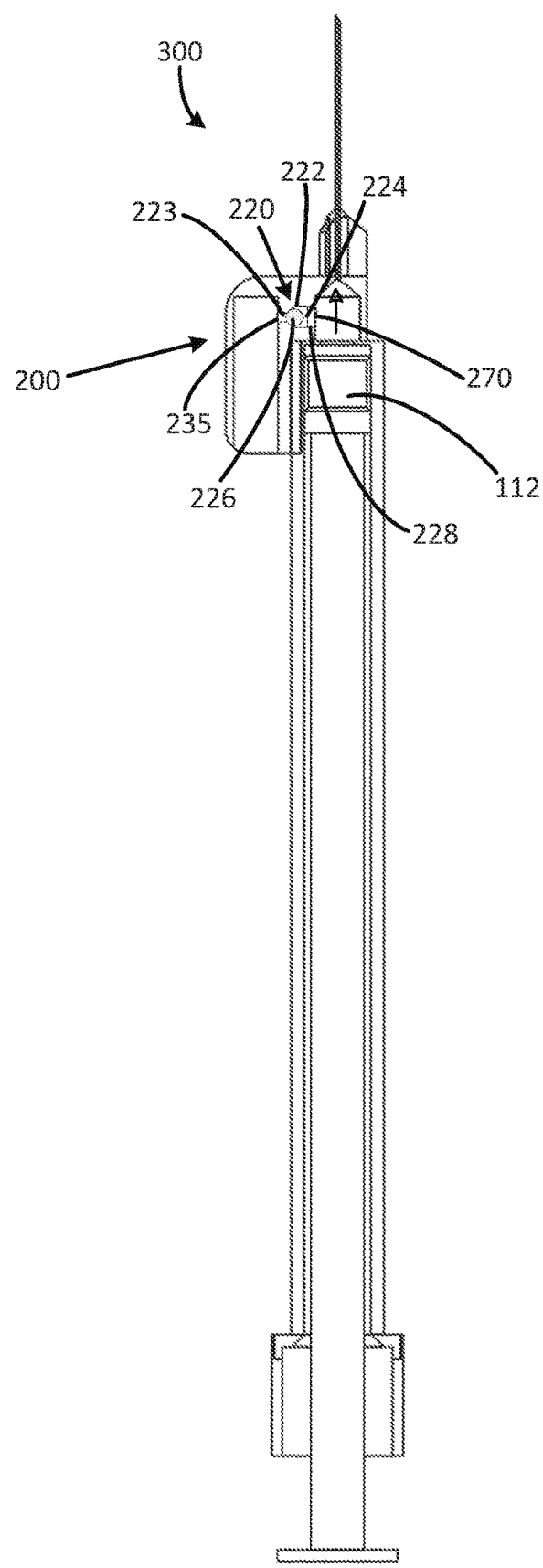
FIG. 7 is a side elevational cross-sectional view of an alternative embodiment of the fluid test device with the plunger in a plunger closed position and with a test module having a valve assembly in an inverted orientation.

With reference to FIG. 7, in contrast to some other embodiments discussed elsewhere herein, some alternative embodiments of the fluid test device 300 may operate such that moving the plunger 112 in a compression stroke allows fluid to enter the test chamber 230, and moving the plunger 112 in a vacuum stroke can prevent fluid from leaving the test chamber 230. There, the valve assembly 220 can be in a closed position while at rest.

In some such embodiments, the valve assembly 220 that is a funnel 222 may operate in the opposite manner as described elsewhere herein. For instance, as shown in FIG. 7, the valve assembly 220 may be positioned such that the narrow end 223 of the funnel 222 is proximal to the aperture and distal to the port while the wide end 224 of the funnel 222 is proximal to the port and distal to the aperture. In this instance, movement of the ball 226 within the funnel 222 can still control the flow of fluid within the funnel 222. The ball stop 228, for example, may be a pin extending through the wide end 224 of the funnel 222 positioned outside of the ball 226. The ball stop 228 may limit movement of the ball 226 in the direction from the narrow end 223 toward the wide end 224 of the funnel 222 while allowing fluid to flow out of the funnel 222. As fluid enters the funnel 222 through the narrow end 223 of the funnel 222, fluid can push the ball 226 toward the ball stop 228, flow over the ball 226, and flow out of the wide end 224 of the funnel 222 to the aperture 235. In contrast, as fluid enters the funnel 222 through the wide end 224 of the funnel 222, fluid can push the ball 226 toward the narrow end 223 of the funnel 222 and be prevented from exiting the funnel 222 through the port 270.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A fluid test device comprising:
   a syringe comprising a barrel and a plunger that is movable in the barrel, the syringe being configured to draw a fluid into the barrel when the plunger is moving from a plunger closed position to a plunger open position and being configured to expel fluid from the barrel when the plunger is moving from the plunger open position to the plunger closed position;
   a test module connectible to the syringe, the test module including a test chamber configured to receive a sample of the fluid from the syringe as the plunger is moving from the plunger closed position to the plunger open position; and
   a test medium contained in the test chamber, wherein when the sample is received by the test module and exposed to the test medium, the test medium is configured to indicate whether the sample comprises at least one of fentanyl and brodifacoum.

2. The fluid test device of claim 1, wherein the test medium comprises a test strip configured to detect the presence or concentration of at least one of fentanyl and brodifacoum in the sample.

3. The fluid test device of claim 2, wherein at least a portion of the test strip is configured to change to a color indicative of the presence or concentration of the at least one of fentanyl and brodifacoum in the sample.

4. The fluid test device of claim 1, wherein the test module has a transparent portion configured to allow viewing of the test medium therethrough.

5. The fluid test device of claim 1, wherein the test chamber is selectively sealable so as to contain the test medium in the test chamber.

6. The fluid test device of claim 1, wherein the test module is configured to prevent the sample from exiting the test chamber as the plunger is moving from the plunger open position to the plunger closed position.

7. The fluid test device of claim 6, wherein the test module further includes a valve assembly configured to control fluid flow into the test chamber, the valve assembly being configured to receive the sample from a port in the fluid test device and feed the sample through an aperture in the test chamber.

8. The fluid test device of claim 7, wherein the valve assembly comprises a check valve positioned between the port and the aperture, the valve assembly having an open position and a closed position, wherein when the valve assembly is in the open position, the sample is configured to flow from the port into the test chamber through the aperture, and wherein when the valve assembly is in the closed position, the sample is prevented from flowing into the test chamber through the aperture.

9. The fluid test device of claim 8, wherein the valve assembly comprises a funnel, a ball, and a ball stop, the funnel having a narrow end and a wide end, the ball being housed within the narrow end and the wide end of the funnel, the ball being configured to prevent the fluid from exiting the funnel through the narrow end of the funnel when the fluid pushes the ball toward the narrow end of the funnel.

10. The fluid test device of claim 1, wherein the test medium comprises an enzyme coating.

11. The fluid test device of claim 1, further comprising an adapter, wherein a portion of the test module is connectable to the adapter.

12. The fluid test device of claim 1, further comprising a reservoir positioned inside the test module, the reservoir being configured to supply the sample to the test chamber.

13. A method for local testing of an injection fluid, the method comprising:
  providing a fluid test device, the fluid test device comprising:
    a syringe comprising a barrel and a plunger that is movable in the barrel;
    a test module connected to the syringe, the test module including a test chamber; and a test medium contained in the test chamber;
  moving the plunger toward a plunger open position to draw the injection fluid into the barrel and to draw a sample of the injection fluid into the test chamber, the test medium indicating information about the sample when the sample is drawn into the test chamber; and
  administering the injection fluid when the at least one of fentanyl and brodifacoum is determined to be absent from the sample.

14. The method of claim 13, wherein the test module prevents the sample from exiting the test chamber after the sample is drawn into the test chamber.

15. The method of claim 13, wherein the test medium comprises a test strip that detects the presence or concentration of the at least one of fentanyl and brodifacoum in the sample.

16. The method of claim 15, wherein at least a portion of the test strip changes to a color indicative of the presence or concentration of the at least one of fentanyl and brodifacoum in the sample.

17. The method of claim 13, wherein the test medium comprises an enzyme coating.

* * * * *